United States Patent
Thibiant et al.

(10) Patent No.: US 6,367,519 B2
(45) Date of Patent: *Apr. 9, 2002

(54) PROCESS FOR FORMING NOVEL SPIRAL COMPOSITIONS

(75) Inventors: Patrick Thibiant, 1475 Via Cresta, Pacific Palisades, CA (US) 90272; Daniel Long; Steven R. Le Cavalier, both of Simi Valley, CA (US)

(73) Assignee: Patrick Thibiant, Pacific Palisades, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/728,818

(22) Filed: Dec. 1, 2000

Related U.S. Application Data

(63) Continuation of application No. 09/481,968, filed on Jan. 12, 2000.

(51) Int. Cl.[7] .............................. B67C 3/26; B67C 3/34
(52) U.S. Cl. ....................... 141/268; 141/100; 141/105; 141/234; 141/279; 141/284; 141/374; 53/237; 53/473
(58) Field of Search ................................ 141/100, 105, 141/234, 267, 268, 279, 284, 374; 53/237, 473

(56) References Cited

U.S. PATENT DOCUMENTS

| | | |
|---|---|---|
| 1,951,694 A | 3/1934 | Goulstone |
| 3,267,971 A | 8/1966 | Mueller |
| 3,509,920 A | 5/1970 | Word |
| 3,559,700 A | 2/1971 | Erickson |
| 4,136,720 A | 1/1979 | Kinney |
| 4,159,028 A | 6/1979 | Barker et al. |
| 4,335,103 A | 6/1982 | Barker et al. |
| 4,881,663 A | 11/1989 | Seymour |
| 4,966,205 A | 10/1990 | Tanaka |
| 5,996,652 A | 12/1999 | Schromm |
| 6,215,166 B1 * | 4/2001 | Thibiant et al. ............... 141/9 |

* cited by examiner

*Primary Examiner*—Timothy L. Maust
(74) *Attorney, Agent, or Firm*—Pillsbury Winthrop LLP

(57) ABSTRACT

A method and apparatus are provided that allows two or more compositions to be filled with a spiral configuration into a single container. Each product may have completely different chemical and physical properties, and each product may have a different function and purpose. The method includes providing at least two compounds, arranged in separate storage bins each having a pump and a hose attached thereto; rotating a container, for receiving a resulting product formed by the at least two compounds, into position relative to a support and alignment funnel; pumping the at least two compounds through the respective hoses into a nozzle assembly having at least two nozzles for filling the container; and combining predetermined amounts of each of the at least two compounds for creating the resulting product housed in a single container, wherein the resulting product has the at least two compounds formed in a spiral configuration.

15 Claims, 3 Drawing Sheets

PROCESS FOR FORMING NOVEL SPIRAL COMPOSITIONS

This is a continuation of application Ser. No. 09/481,968 filed on Jan. 12, 2000.

BACKGROUND OF THE INVENTION

1. Area of Art

The present invention relates to making multi-product fills for substantive and decorative purposes. In particular, the present invention relates to novel ways to fill containers with separate kinds and types of cosmetics, whereby an enhanced and durable spiral configuration of multi-phase (heterogeneous) products may be made, in addition to other novel product configurations.

2. Description of the Prior Art

A survey of existing products on the market reveals the multiple efforts that have been made to create visually appealing product configurations, and the containers that house them, which serve to preserve a desired visual appeal. Likewise, in addition to mechanical attempts to solve these problems, chemical solutions have also been attempted; however, the lack of commercial success in this field points to an on-going and longstanding need.

Conventional attempts at making a two-or-more phase product in one dispensing container have proven difficult and sometimes impossible due to chemical reactions or product instability (i.e., reacting with each other). What has not been adequately accomplished, or developed to date, is a system based on the chemicals themselves and the system chemistry and incompatibility—for example, putting water and oil together. Likewise, after reviewing thousands of products, only a few personal care cosmetics with two-or-more phases in one dispensing container were uncovered.

To understand why known systems have not been able to address the aforementioned problems effectively, further background is offered for consideration to explain the nature of the problem, and why it has been solved by the instant teachings.

Cosmetic materials generally contain various types of coloring materials, such as pigments and dyes. Such coloring may materials contain materials derived from raw materials as maskimg agents for covering coloring. In some cases, these masking agents are included for the purpose of providing a particular effect in relation to skin makeup. Such effect is a positive function of these coloring materials.

Because consumers have increasingly demonstrated a diverse sense of appreciation in regard to the value of cosmetic materials, such cosmetic materials are now required to possess additional merits related to their intrinsic appeal as objects of beauty. This appreciation is in complement with providing pleasure in use, as well as the basic functions of being suitable for make-up, and so forth. In other words, today's cosmetics must look good and work well to satisfy the needs of the consumers.

Historically, the preparation of two-or-more differently colored products has been challenging. Even in cosmetics such as basic lipsticks, to produce a two-tone or multi-colored effect on the lips required innovation. In such instances, to achieve the desired blending effect, one color had to be applied to the lips as a base and the other color or colors superimposed thereon for contrast. The desired final effect was then achieved by blending the superimposed colors on the lips itself.

Likewise, attempts have been made to produce a unitary lipstick having a plurality of colors by assembling several individual segments in an adjacent spaced relationship, and thereafter compressing the segments together to form a unitary lipstick mass. Such lipsticks, however, have met with limited commercial success. One reason may be that these lipsticks have been more difficult and expensive to produce than conventional one-color lipsticks. In practice, of course, lipsticks that are formed by molding segments of different colors into a single multi-colored tube are usually applied to the lips by using the single color of each segment such that these lipsticks merely offer the convenience of two separate colors in one unitary mass.

Known disclosures thus highlight that the concept of a dual-phase or multi-phase cosmetic composition being quite interesting inasmuch as such a composition has a potential for combining two or more functional cosmetic aspects into a single product that may be applied to a subject. However, with any such multi-functional, multi-phase cosmetic composition, it is obviously important that the formed product be functional and effective and that such be maintained, preserved, and usable over a reasonable product life span. This difficulty has not been overcome by known disclosures.

Another largely unaddressed issue is containing and packaging a multi-phase cosmetic composition. Here, it is desirable that each of the phases comprising the total product be dispensed into a container such that the respective phases are generally maintained separately, remain stable, and that in viewing the product, each phase as packaged is visually distinct. Of principal concern is that during the proposed life of a multi-phase cosmetic product, respective phases comprising the total product do not blend and mix together such that the total product in the end is nearly or substantially homogeneous. In addition, in containing a multi-functional, multi-phase cosmetic composition, it is important that the respective phases comprising the composition be dispensed in a manner such that the particular phases are present and occur throughout the final product. It is also important that in gathering a single application from a container, a subject is likely to gather an adequate amount of each respective phase.

At the root of these several matters is the idea that cosmetic products rely on color to provide beauty enhancement. Thus, beauty aids such as foundation, blush, mascara, brow products, and the like, rely on color enhancement provided by these products for effectiveness. In view of the criticality of color in such applications, it is desirable to present the cosmetic product, which is ultimately applied to the face or other parts of the body to highlight that color, in a way that emphasizes its color. In the past, such cosmetic products, if visible at all, were presented as a colored composition. Those skilled in the cosmetic arts appreciate that if the color of the cosmetic composition could be presented in a more dramatic manner, the product would be more desirable to the purchaser.

For example, presenting the color in the form of a spiral, helix, swirled pattern, or the like, against a background of a clear or color-contrasted liquid, dramatically emphasizes the attractiveness of the color of the cosmetic beauty aid.

It would be relatively simple to produce an oil-based pigment phase in a clear aqueous phase, or vice versa. The immiscibility of the two phases would permit the production of a cosmetic product in which the above desired, highly attractive packaging could be provided. However, the inclusion of an oil-based phase would be undesirable for at least two reasons. First, it would be difficult to combine the immiscible phases to form the complete cosmetic composition. Second, even if the two immiscible phases could somehow be combined, the product, containing a non-water-soluble phase might be difficult to remove.

Ideally, a two-phase composition should include a color phase and clear or color-contrasted gel phase that are miscible. However, when attempts were made to produce such a product in the past, a two-phase composition was obtained in which the color phase bled into the gel phase, producing a product that was aesthetically unattractive.

Thus, cosmetic products have not been produced in which a color phase, highlighting the tint or color of the cosmetic composition, is disposed as a discrete color phase against a background of a clear or color-contrasted gel.

An emulsion is known to be a dispersed system comprising at least two immiscible liquid phases (*Remington's Pharmaceutical Sciences*, 18th Edition, 1990). The emulsion's immiscible liquid phase is composed of droplets between 0.005 to 2000 microns in diameter, although the range of droplet diameters may be narrower (e.g., between 0.1 to 100 microns). Emulsions are known to be thermodynamically unstable. It is believed that the free energy associated with the high surface area of small droplets is reduced when these droplets coalesce into large droplets of less surface area. To minimize droplet coalescence, it is known that an emulsifying agent can be added to form a thin film about each droplet of immiscible liquid in the emulsion (*Remington's Pharmaceutical Sciences,* 18th Edition, 298–309, 1990).

Stable emulsions containing silicones of two or three phases are well-known. The low surface tension of silicone promotes thin film formation which stabilizes emulsions. Lower alkyl ($C_1$–$C_4$) and amino-substituted polysilaxanes (silicones) are used because of their insolubility in polar and non-polar liquids such as water and oils. Seldom used are the cyclic silicones, such as diphenylmethicone, because of their oil solubility which causes the cyclic silicones to dissolve in the oil phase of the emulsion rather than forming a distinct phase.

Silicone emulsions have been used in a number of products. In cosmetic, pharmaceutical and skin preparations, a fat paste-like emulsion of decamahylpentasilaxune, poly (oxyethylene stearate), water and sorbitan monostearate has been used (Thimineur R. J. & Traver F. J., DE 3,045,083). In personal-care formulations, such as water-based hair conditioners, water in silicone emulsion has been used (Gum, M. L., W08S/03641/AI). In formulations for polishes, an emulsion of dimethylsiloxanes, naphtha hydrocarbons, emulsifiers and water has been used (Hill M. P. L. & Vandamme L. J R., DE 3,616,575 A1). Water-thinned paint emulsions have used silicones (Udalova A. V., et al.,*Lakokas Mater, Ikh. Primen.,* 2:14–16). Waterproof sealant emulsions have used silicones (Saad W. T. & Stodgell R. F., U.S. Pat. No. 4,383,06; Bauman T. M., Freiberg A. L., U.S. Pat. No. 4,590,220).

The ordered phase of liquid crystal has many of the properties of the solid state such as optical anisotropy and birefringence, which produce special interference patterns that can be detected using a cross-polarizing microscope. Liquid crystals also have the mechanical properties of liquids. Because the crystals have only partial rotational or translational freedom the liquid crystals exist in a mesophase state (*Intro to Liquid Crystals*, Priestly E. B., et al., eds., Plenum Press, N.Y. 1976).

Liquid crystals known as lyotropic liquid crystals may spontaneously form when the concentration of oils in an oil-water emulsion is at a particular concentration. (See, e.g., Marland J. S. & Mulley B. A., *J. Pharm. Pharmocol.* 1971, 23(8): 561–572). Lyotropic liquid crystal formation is commonly observed in a wide variety of emulsions and such liquid crystals are known to be unstable.

The only significant attempt among the prior art to address the problem solved by the teachings of the present invention was a hair gel where a white product was filled inside of a clear gel. The product was filled using a two-step process. First, the clear gel was filled with an Arenco tube, and then in a modified registration station, the spiral was filled with a diving nozzle and a peristaltic pump.

Formation of the spiral required spinning the tube of clear gel and then submerging the nozzle to the bottom of the tube. While the nozzle was then lifted up, the peristaltic pump started and operated until the nozzles came close to the top of the clear product. The next step was stopping and reversing to stop the flow of the white product.

Known spiral fills (for example sold by Estee Lauder[7], Lapraire[7], Erno Lazlo[7] and Revlon[7]), or more elaborate designs in clear gel, are priced at between $50.00 and $100.00, and require two-step processes, both of which urge strongly against their industrial efficacy. Their respective shelf-lives are also dubious.

Likewise, toothpaste-tube filling technology works by simultaneously filling tubes in straight lines that show through transparent windows in the sides of the tubes. While such efforts are dictated by ornamental constraints, no known methods can perform the process in fewer than two steps.

Finally, there are liquid crystals that form at only certain temperatures known as thermotropic liquid crystals. This type of liquid crystal is quite stable, but has not been used to solve the problems addressed by the teachings of the present invention.

U.S. Pat. No. 4,335,103 to Barker et al. (the '103 patent) discloses a two-phase cosmetic cleansing cream composition that includes two separate and stable cosmetic composition phases that, when inter-mixed, yield a cleansing composition that is applicable to the face and other parts of the body. This composition comprises a first cleansing-cream phase composition that includes an oil, a thickening agent, an emulsifier, and water.

The second phase, a gel phase, comprises water or a water-soluble material and a thickening agent. The two-phase cosmetic cleansing cream compositions are combined in a swirl-like or marble-like pattern within a container such that the cream hard-gel phases are generally stable, separate, and visibly distinct.

Although the teachings of the '103 patent represents an advance in the art, it does not emphasize a color phase. Colorants easily migrate. As such, the absence of a teaching in the prior art of non-bleeding phases establish the absence in the art of a two-phase cosmetic composition in which the color-phase composition highlights the critical emphasis of the composition.

Likewise, conventional cosmetic vehicles for skin moisturization deliver moisture to the skin only on the initial application of the cosmetic moisturizer. The need for a cosmetic, dermatologic or medicinal multi-phasic vehicle that will, in addition, provide sustained skin moisturization while blocking skin moisture loss has been long felt. There has also been a need for a multi-phase vehicle that can be used to provide water-soluble and lipid-soluble active ingredients, such as vitamins, plant extracts, antioxidants, proteins, polymers, oils and the like. Most cosmetic vehicles consist of emulsions. In sum, there are needs for two or more types of cosmetic products housed within the same container.

In contrast to known systems, the teachings of the present invention address and overcome these long felt needs by providing, instead of two or more different products, one product (or a unitary composition housed in a single container) with multiple functions and different appearances.

The present inventors have yet to see something functional like this on the market. There are some products with somewhat similar concepts, but not functionally implemented. Attempts ranging from products with floating materials that have no purpose to spirals that degrade when moved, or merely constitute ornamental fillers, show the need for the present invention. Accordingly, the instant system combines chemical functionality and a visually appealing product to overcome the drawbacks of the prior art.

OBJECTS AND SUMMARY OF THE INVENTION

Accordingly, it is an object of the present invention to provide a process and apparatus to overcome the drawbacks of the prior art.

Additionally, it is an object of the present invention to provide a process and apparatus for generating a dual-phase or multi-phase product whereby each phase maintains certain chemical and physical properties that makes each phase stable and gives each phase the ability to co-exist with the other.

Another object of the present invention is to provide a solution to the problem of having multiple functions in a single product by creating a stable and extremely functional product.

Briefly stated, an apparatus is provided that can have two or more products filled in the same container having a swirl-like pattern. Each product can have completely different chemical and physical properties. Thus, each product can have a different function and purpose.

According to an embodiment of the present invention, there is provided a method of forming spiral compositions, comprising the steps of: providing at least two compounds, arranged in separate storage bins each having a pump and a hose attached thereto; rotating a container, for receiving a resulting product formed by the at least two, into position relative to a support and alignment funnel; pumping the at least two compounds through the respective hoses into a nozzle assembly having at least two nozzles for filling the container; and combining predetermined amounts of each of the at least compounds for creating the resulting product housed in a single container, wherein the resulting product has the at least two compounds formed in a spiral configuration.

According to an embodiment of the present invention, there is provided an apparatus for filling a container with a resulting product having at least two compositions formed in a spiral configuration, comprising: a nozzle assembly having at least two nozzles coupled together in a close configuration; at least two pumps for pumping each of the compositions stored in separate composition storage bins each interconnected by a suction hose to each pump; at least two hoses interconnected to the nozzles and the pumps; a support and alignment funnel coupled to the apparatus for supporting the container to be filled in an upright position; a drive motor coupled to the nozzle assembly adapted to move the nozzle assembly in a vertical direction during filling of the container; and a spinning motor coupled to a spinning puck that supports the container and rotates the container during filling of the container.

DETAILED DESCRIPTION OF THE INVENTION

Figure 1:
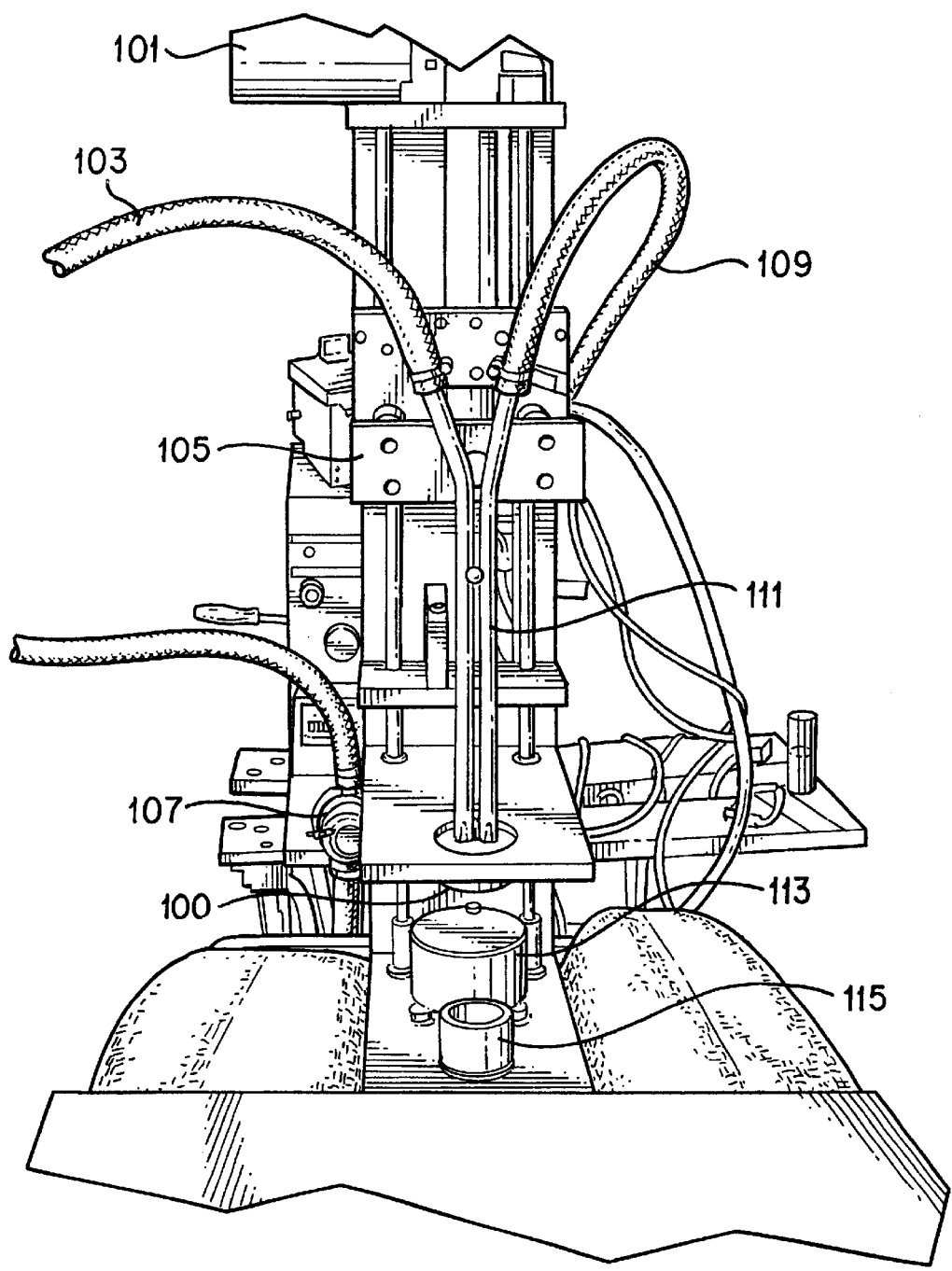
FIG. 1 illustrates a front view of an apparatus that performs the process of creating at least a dual-phase spiral product according to an embodiment of the present invention.

The present inventors have discovered that, as discussed above, one approach not adequately explored to date involves a new delivery system using a toothpaste-like filling concept, with one of the two usual steps eliminated, and applying the same to a desired personal care product. This invention allows the generation of a wide variety of products, especially those nearly impossible to formulate with chemicals or alternate systems (i.e., ascorbic acid or clear shower gel with a high level of silicones).

The present inventors have further discovered that dual-phase compositions are most favorably disposed within single containers for many cosmetic industry applications. In solving the problems discussed above with respect to creating chemically integrable products, issues with respect to filling containers with the resulting compositions have generated their own respectively innovative solutions.

Namely, in lieu of rotating tubes, top and bottom filling schemes, and control rate of flow issues, the present inventors have fabricated a one-step process that allows the filling of a product having two or more compounds with ratios and patterns that are quite variable, yet makes a durable resulting product.

Likewise, the flexibility achieved by the instant teachings has resulted in a novel enhanced spiral fill that overcomes the pitfalls created as artifacts of the toothpaste-based processes. This approach enables the dispensing of the product in a more uniform and aesthetically-pleasing fashion, in addition to an improved display.

As mentioned below, the most studied prior art attempt to address the problem solved by the teachings of the present invention was a hair gel where a white product was filled inside of a clear gel. The product was filled using a two-step process. First, the clear gel was filled with an Arenco tube, and then in a modified registration station, the spiral was filled with a diving nozzle and a peristaltic pump.

According to this disclosure, formation of the spiral required spinning the tube of the clear gel and then submerging the nozzle to the bottom of the tube. While the nozzle was then lifted up, the peristaltic pump started and operated until the nozzle came close to the top of the clear product. The next step was stopping and reversing the flow of the white product. In addition to the cost factors, high degrees of mechanical and systemic failures resulted from this two-step process.

Conventional spiral fills have been subject to these same constraints, and by way of further example, known designs in clear gel are priced at between $50.00 and $100.00, per container and require two-step processes, both of which urge strongly against their industrial efficacy. This is in addition to the fact that such disclosure has little durability.

Similarly, and in contrast to the instant teachings, toothpaste-tube filling technology works by simultaneously filling tubes in straight lines that show through transparent windows in the sides of the tubes. While such efforts are dictated by ornamental constraints, neither method can perform the process in fewer than two steps.

FIG. 1 illustrates a front view of an apparatus that performs the process of creating at least a dual-phase spiral product according to an embodiment of the present invention. A drive motor dive assembly 101 is shown, which is coupled to the filling nozzle assembly 111. The drive motor dive assembly 101 is adapted to move the filling nozzle assembly 111 in a vertical direction for filling a container with the resulting product. FIG. 1 illustrates a nozzle assembly 111 having two nozzles, but, there may be more than two nozzles incorporated into a nozzle assembly 111 depending upon the resulting product to be created. The nozzle assembly 111 may be further supported by a nozzle support assembly 105 coupled to the apparatus.

FIG. 1 also illustrates a spinning motor 113, arranged next to a spinning puck 115, that is underneath a support and alignment funnel 100. The support and alignment funnel 100 and the spinning puck 115 hold up the container (or tube) during the filling process. The spinning puck 115 is driven by the spinning motor 113, which provides the mechanical capability to rotate the spinning puck 115, thus rotating the container, during the filling process.

There are also pumps 107, 135 (see FIG. 2) for pumping each of the compositions (that will form the resulting product) stored in separate composition storage bins through hoses 103, 109 that are interconnected to the pumps (107, 135) and the nozzle assembly 111. The pumps may be gear-type pumps, or piston-type pumps. Preferably, piston-type pumps are used because they provide a more precise delivery of the compositions stored in the storage bins.

Figure 2:
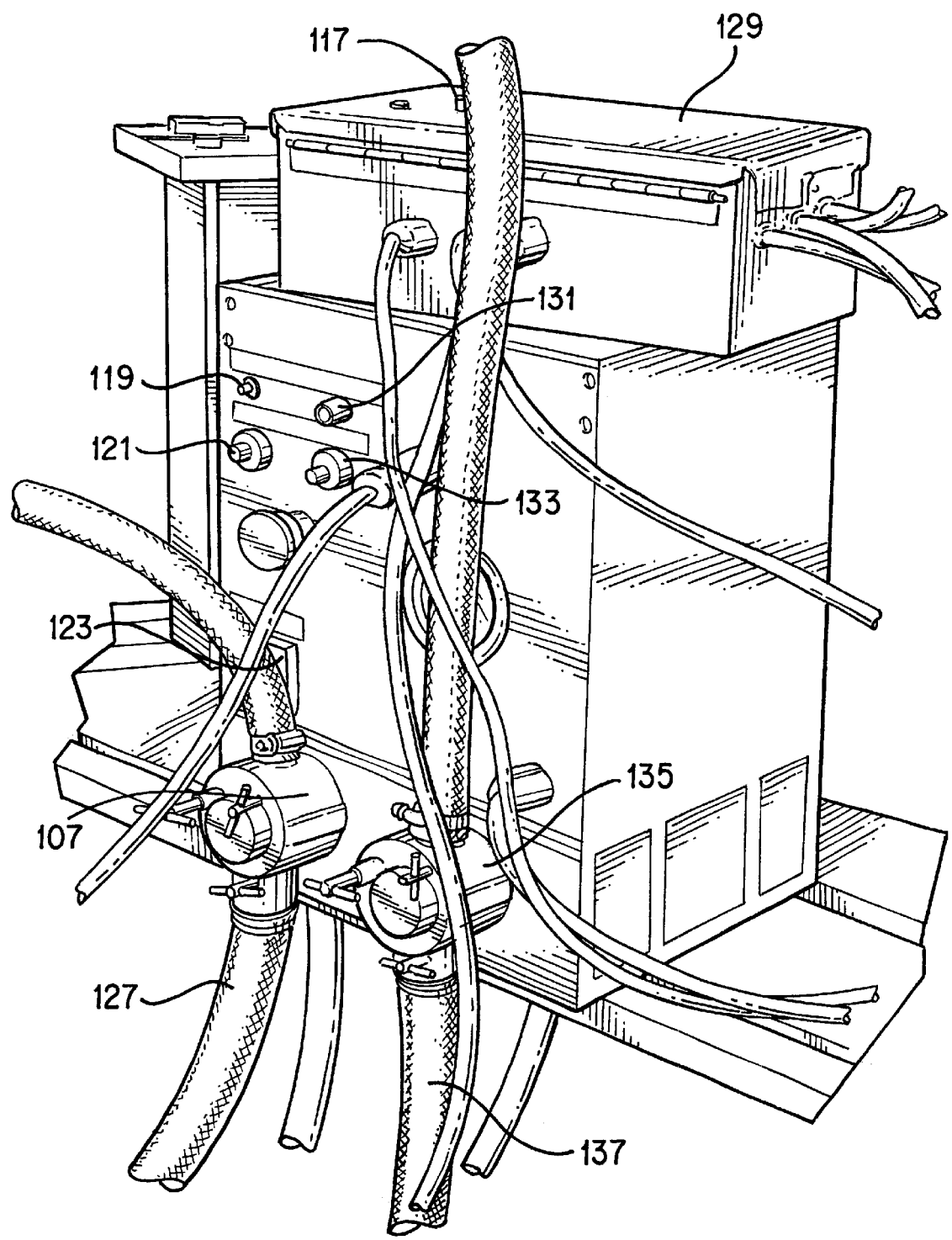
FIG. 2 illustrates a rear view of an apparatus having a control mechanism that performs the process of creating at least a dual-phase spiral product according to an embodiment of the present invention.

FIG. 2 illustrates a rear view of an apparatus having a control mechanism that performs the process of creating at least a dual-phase spiral product according to an embodiment of the present invention. The first pump 107 and a second pump 135 are shown at the rear of the apparatus. Connected to the pumps 107, 135 are suction hoses 127, 137, which are interconnected with the separate composition storage bins.

FIG. 2 illustrates a flow rate controller 121, 133 for controlling the flow rates of each of the pumps 107, 135. A fill-time timer 123 is provided on the apparatus to determine the amount of time required to fully fill a container of the resulting product. There is also a spin speed controller 117 on the apparatus to control the rotational velocity of the spinning puck 115. A dive and rise after fill speed controller 119 allows the user to control the speed of the nozzle assembly 111 as it moves in the vertical direction before and after the filling operation. The control box for lifting and spinning 129 houses the electronics and circuitry for controlling the spinning motor 113 and the drive motor dive assembly 101. There is also a rise during fill speed controller 131 on the apparatus that allows the user to control the speed of the nozzle assembly as it moves up in the vertical direction during the filling operation.

Figure 3:
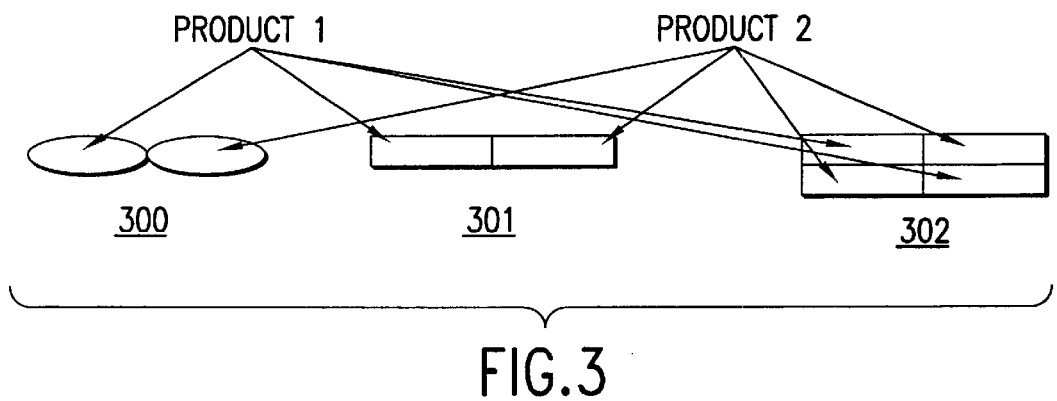
FIG. 3 illustrates a cross-sectional view of three examples of nozzle configurations according to an embodiment of the present invention.

FIG. 3 illustrates a cross-sectional view of three examples of nozzle opening configurations 300, 301, 302, each producing a dual-phase composition according to an embodiment of the present invention. Each of these three nozzle opening configurations 300, 301, 302 will produce a resulting product with different spiral configurations. The arrangement of the nozzle openings with the type of material to be dispensed may be of a variety of combinations, and FIG. 3 illustrates only three exemplary samples.

Figure 4:
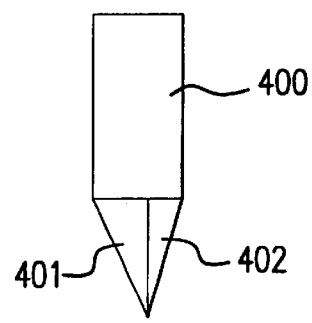
FIG. 4 illustrates a side view of an example of an opening of a nozzle assembly according to an embodiment of the present invention.

FIG. 4 illustrates a side view of an example of an opening of a nozzle assembly 111 according to an embodiment of the present invention. For example, a clear gel may be dispensed from the center of the nozzle 400, while colored/contrast materials may be dispensed from the nozzle openings on the sides 401, 402. Any suitable arrangement may be made in order to produce a specific spiral configuration of the resulting product.

The compounds and compositions dispensed by the apparatus of the present invention are not limited to cosmetic and/or health care products. Any liquid or semi-liquid compound may be dispensed from the storage bins, including different colored waxes for making candles having novel spiral configurations. Plastics and other polymer materials may also be dispensed, and novel spiral configurations may also be formed by the apparatus of the present invention using these materials.

Having described preferred embodiments of the invention with reference to the accompanying drawings, it is to be understood that the invention is not limited to those precise embodiments, and that various changes and modifications may be effected therein by one of ordinary skill in the art without departing from the scope or spirit of the invention as defined in the appended claims.

What is claimed is:

1. An apparatus for filling a container with a resulting product having at least two compositions formed in a spiral configuration, comprising:

a nozzle assembly having at least two nozzles coupled together in a close configuration;

at least two pumps for pumping each of the compositions stored in separate composition storage bins, each bin being connected to one of the pumps by a suction hose;

hoses connecting the nozzles to the pumps;

a support and alignment funnel coupled to the apparatus for supporting the container to be filled in an upright position;

a drive motor coupled to the nozzle assembly adapted to move the nozzle assembly in a vertical direction during filling of the container; and a spinning motor coupled to a spinning puck that supports the container and rotates the container during filling of the container.

2. The apparatus for filling a container with a resulting product according to claim 1, wherein the resulting product is a dual-phase composition.

3. The apparatus for filling a container with a resulting product according to claim 1, wherein the resulting product is a multi-phase composition.

4. The apparatus for filling a container with a resulting product according to claim 1, wherein the resulting product is at least one of a facial cosmetic treatment and a cosmetic treatment for the body.

5. The apparatus for filling a container with a resulting product according to claim 1, wherein the resulting product is a cationic personal care product.

6. The apparatus for filling a container with a resulting product according to claim 1, wherein the resulting product is a non-ionic personal care product.

7. The apparatus for filling a container with a resulting product according to claim 1, wherein the resulting product is a body gel.

8. The apparatus for filling a container with a resulting product according to claim 1, wherein at least one of the two compositions is a wax.

9. The apparatus for filling a container with a resulting product according to claim 1, wherein the at least two pumps are gear pumps.

10. The apparatus for filling a container with a resulting product according to claim 1, wherein the at least two pumps are piston pumps.

11. An apparatus for filling a container with at least two compounds, said apparatus comprising:

storage bins for storing the compounds;

means in flow communication with the bins for pumping each of the compounds from said bins;

a nozzle assembly having a plurality of nozzles, the nozzles being in flow communication with the pumping means;

first support means coupled to the apparatus for supporting the container in an upright position; and second support means disposed adjacent the container for supporting a turning motion thereof, wherein the apparatus is configured to produce a resulting product that is at least a dual-phase composition having a generally swirled, spiral configuration.

12. The apparatus of claim 11, wherein the means for pumping is selected from the group consisting of gear pumps and piston pumps.

13. The apparatus of claim 11, wherein the resulting product is a candle, or a composition selected from the group consisting of a facial cosmetic treatment, a cosmetic treatment for the body, a cationic personal care product, a non-ionic personal care product, a body gel, and combinations thereof.

14. The apparatus of claim 13, wherein the resulting product has more than two distinct phases.

15. The apparatus of claim 13, wherein the compounds are selected from the group consisting of a wax, a gel, a cream, and a plastic.

* * * * *